US008312899B2

(12) United States Patent
Zucchi et al.

(10) Patent No.: US 8,312,899 B2
(45) Date of Patent: Nov. 20, 2012

(54) HOSES WITH CONNECTION PORTIONS

(75) Inventors: Giuseppe Zucchi, S. Possidonio (IT); Daniele Resca, San Felice sul Panaro (IT); Tamara Baraldi, San Felice sul Panaro (IT)

(73) Assignee: Covidien AG, Neuhausen am Rheinfall (CH)

( * ) Notice: Subject to any disclaimer, the term of this patent is extended or adjusted under 35 U.S.C. 154(b) by 547 days.

(21) Appl. No.: 12/434,231

(22) Filed: May 1, 2009

(65) Prior Publication Data

US 2009/0301593 A1 Dec. 10, 2009

(30) Foreign Application Priority Data

Jun. 10, 2008 (EP) .................................... 08425410

(51) Int. Cl.
*F16L 11/00* (2006.01)

(52) U.S. Cl. ......................... 138/122; 138/109; 138/132

(58) Field of Classification Search .................. 138/122, 138/109, 132

See application file for complete search history.

(56) References Cited

U.S. PATENT DOCUMENTS

| | | | | | |
|---|---|---|---|---|---|
| 2,396,059 | A * | 3/1946 | Roberts | ........................ | 138/122 |
| 2,927,625 | A | 3/1960 | Rothermel et al. | | |
| 3,416,982 | A * | 12/1968 | Petzetakis | .................... | 156/193 |
| 3,890,181 | A * | 6/1975 | Stent et al. | .................... | 156/143 |
| 3,938,929 | A * | 2/1976 | Stent et al. | .................... | 425/501 |
| 4,343,672 | A * | 8/1982 | Kanao | .......................... | 156/428 |
| 4,490,575 | A * | 12/1984 | Kutnyak | ........................ | 174/47 |
| 4,870,535 | A * | 9/1989 | Matsumoto | .................. | 361/215 |
| 5,555,915 | A | 9/1996 | Kanao | | |
| 6,024,134 | A * | 2/2000 | Akedo et al. | .................. | 138/129 |
| 6,305,428 | B1 | 10/2001 | Nakamura et al. | | |
| 7,631,667 | B2 * | 12/2009 | Brink et al. | .................. | 138/109 |
| 2002/0003003 | A1 * | 1/2002 | Hayashi et al. | ............... | 138/127 |
| 2010/0108170 | A1 * | 5/2010 | Chudkosky et al. | .......... | 138/122 |

FOREIGN PATENT DOCUMENTS

| | | | |
|---|---|---|---|
| GB | 1 064 615 | A | 4/1967 |
| WO | WO 2005/098302 | A | 10/2005 |

OTHER PUBLICATIONS

European Search Report for Appln. No. 08 42 5410 dated Dec. 12, 2008.

* cited by examiner

*Primary Examiner* — James Hook

(57) ABSTRACT

A hose consisting of a smooth tubular wall and a rib wound spirally on the smooth tubular wall. The hose includes at least one duct portion and at least one connection portion; in the connection portions, the rib is wound spirally with a narrower pitch than on the duct portions.

13 Claims, 1 Drawing Sheet

5 1 3 2 4 4

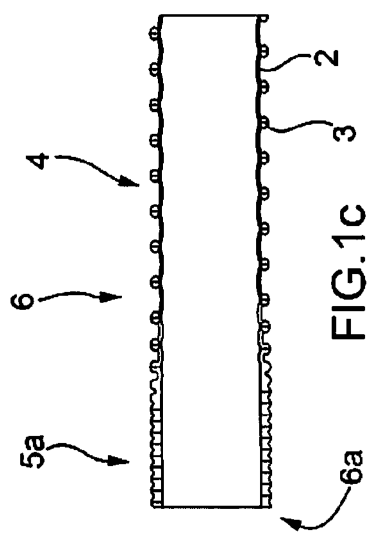
FIG.1c
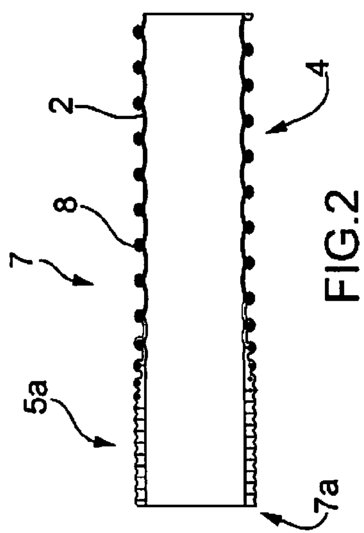
FIG.2
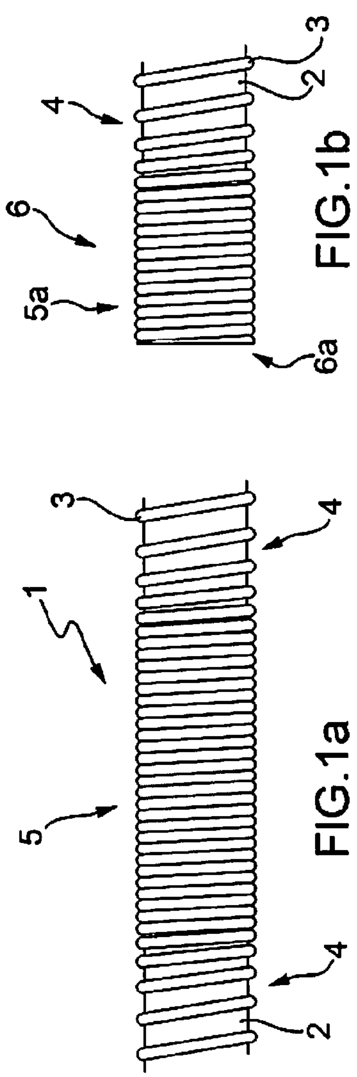
FIG.1b
FIG.1a
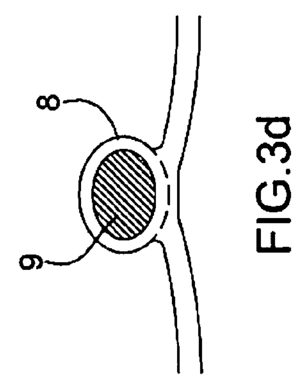
FIG.3d
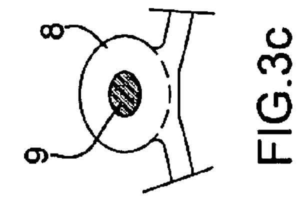
FIG.3c
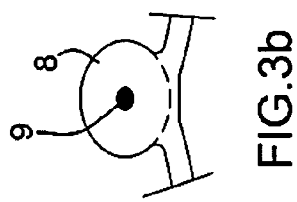
FIG.3b
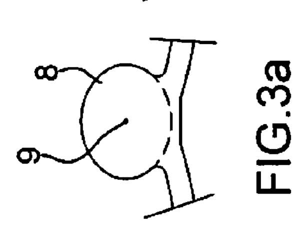
FIG.3a

HOSES WITH CONNECTION PORTIONS

TECHNICAL FIELD

The present disclosure relates to hoses with connection portions. In particular, the present disclosure refers to respiratory circuit tubes to which the description explicitly refers without loss of generality.

BACKGROUND OF THE INVENTION

Respiratory circuits are used to interface in a flexible manner the tracheal or tracheostomic tube of a patient to a ventilation system.

Currently, the types of tubes used for these purposes are spiral tubes, generally made of PVC and consisting of a flexible flat part and a rigid reinforcement rib wound in a continuous spiral or corrugated tubes. The corrugated tubes are generally made of continuously blown polyethylene or polypropylene and provided with inserts to facilitate the connection to dedicated fittings, or extensible tubes which are generally made of continuously blown polypropylene and provided with inserts to facilitate connection to dedicated fittings. The latter are supplied packed.

Condensation may form in respiratory circuit tubes and this represents a vehicle for the bacteria present inside the patient and the circuit itself, in addition to constituting a serious danger for the patient as it can get into the lungs, preventing correct functioning thereof. In this regard, the type of tubes commonly utilized are spiral tubes, as they have transparent walls and, since the walls are smooth, there are no dead areas that can favour the accumulation of condensation, a phenomenon which occurs, on the other hand, in corrugated tubes.

Generally, spiral tubes have flexible terminal connections which are applied to fittings by means of solvent gluing.

The object of the present disclosure is to produce spiral tubes having terminal connection portions that do not require gluing for application to the fittings.

SUMMARY

In accordance with the present disclosure, a hose is provided which includes a smooth tubular wall and a rib wound spirally on the smooth tubular wall; wherein the hose includes at least one duct portion and at least one connection portion; wherein in the connection portions, the rib is wound spirally with a narrower pitch than in the duct portions.

In one aspect, the pitch of the spirally wound rib is reduced to a minimum, to about zero.

In another aspect, the spirally wound rib includes a core made of rigid material.

BRIEF DESCRIPTION OF THE DRAWINGS

Various embodiments of the present disclosure will be described herein below with reference to the figures wherein:

FIG. 1*a* illustrates a tube according to the present disclosure as produced by the extruder;

FIG. 1*b* illustrates a tube obtained from the tube illustrated in FIG. 1*a;*

FIG. 1*c* is a longitudinal cross section of the tube of FIG. 1*b;*

FIG. 2 is a longitudinal cross section of a tube according to a further embodiment of the present disclosure; and FIGS. 3*a*-3*d* are respective four sections of the rib of the tube of FIG. 2.

DETAILED DESCRIPTION

In embodiments, a hose or tube 1 in accordance with the present disclosure is illustrated in FIG. 1*a*. The tube 1 may be produced by means of extrusion and may include a smooth tubular wall 2 and a rib 3 made of the same material as the tubular wall 2. The rib 3 may be wound spirally around the smooth tubular wall 2 of tube 1.

The tube 1, as obtained by the extruder, may include a succession of duct portions 4 and connection portions 5, only one of which can be seen in FIG. 1*a*. Each of the duct portions 4 may have a constant pitch different from zero, while each of the connection portions 5 may include a rib 3 wound spirally with a pitch reduced to a minimum, of about zero.

In FIGS. 1*b* and 1*c*, tube 6 may be obtained from the tube 1 following a cutting operation in the connection portions. In this way, the tube 6 produced may include a connection portion 5*a* deriving from a part of the connection portion 5 of the tube 1, and arranged at one end 6*a* of the tube 6 so that it may connect directly to the connector elements of a respiratory circuit.

As illustrated in FIG. 1*c*, reducing the pitch of the rib 3 of the connection portions 5 and 5*a* to a minimum, of about zero, results in a thickening of the wall of the tube.

In embodiments, a tube 7 in accordance with the present disclosure is illustrated in FIG. 2. The parts of the tube 7 are equivalent to those of the tube 1 and are indicated by the same numbering, not requiring an additional description herein.

However, in embodiments, tube 7 may include a different structure of the rib. The rib 8 present in the duct portions 4 may include a rigid core 9. In particular, as shown in FIG. 2 and as illustrated in detail in FIGS. 3*a*-3*d*, the thickness of the rigid core 9 may increase as it moves away from the connection portion 5*a* located at one end 7*a* of the tube 7. More specifically, the rib 8 in duct portions 4 may have a rigid core 9 with a very small diameter (see FIG. 3*a*) which may increase (see FIGS. 3*b*-3*d*) as it moves towards the inside of the duct portion 4 where, once a certain dimension has been reached, it remains constant.

In embodiments, the tubes according to the present disclosure may be produced by extrusion using three different extruders. A first extruder may be responsible for the extrusion of tubular wall 3, while a second and a third extruder may be respectively responsible for the extrusion of rigid core of the rib and of outer part of the rib. In particular, by changing the speed of an extruder screw of the second and the third extruders, it is possible to dose the quantity of both the rigid core material and the outer material of the rib, while maintaining unchanged the rib external diameter. In other words, the combination of the co-extrusion variability together with a variable pitch mandrel, allows a progressive decrease of pitch during extrusion without stops coupled with decrease of rigid core screw velocity and increase of soft material screw velocity.

The tubes of the present disclosure may have the same properties as the hoses of the prior art, including rigidity and flexibility of the different portions of the tube itself.

However, the tubes of the present disclosure do not require the use of specific fittings for their assembly in the respiratory circuit and, therefore, do not require gluing operations. In fact, the tubes subject of the present disclosure permit assembly of the circuits by means of a simple insertion operation. Furthermore, the tubes subject of the present disclosure can be made of materials different from PVC. Lastly, once the tube including a plurality of connection portions has been produced by extrusion, tubes can be produced with the terminal connection portion of the required length according to where the cut is made.

The invention claimed is:

1. A hose comprising:

a tubular wall including at least one duct portion having a longitudinal axis when in a straightened configuration;

a rib wound spirally on the tubular wall at a first pitch along the at least one duct portion, the rib forming at least one connection portion without requiring additional longitudinally extending structure therefrom, wherein the rib which forms the at least one connection portion is wound at a second pitch which is narrower than the first pitch; and the rib including a core of rigid material, the core of rigid material increasing in diameter away from the at least one connection portion and toward the at least one duct portion.

2. The hose according to claim 1, wherein the pitch of the at least one connection portion is reduced to a minimum, to about zero.

3. The hose according to claim 2, wherein the pitch of the at least one connection portion forms a thickening of the tubular wall of the hose.

4. The hose according to claim 1, wherein the pitch of the at least one duct portion includes a constant pitch not equivalent to zero.

5. The hose according to claim 1, wherein the at least one connection portion is configured to connect to a connector element of a respiratory circuit.

6. The hose according to claim 1, wherein the rigid material is present at least in the at least one duct portion.

7. The hose according to claim 6, wherein the diameter of the rigid material remains constant once a certain dimension has been reached.

8. The hose according to claim 1, wherein the hose is formed via a cutting operation in the at least one connection portion.

9. The hose according to claim 1, wherein the at least one duct portion and the at least one connection portion each have a different rigidity.

10. The hose according to claim 9, wherein the at least one duct portion has a greater rigidity than the at least one connection portion.

11. The hose according to claim 1, wherein the rib is formed on an outer portion of the tubular wall.

12. The hose according to claim 1, wherein the rib defines a corrugation along at least a portion of the tubular wall.

13. A hose comprising:

a tubular wall including at least one duct portion having a longitudinal axis when in a straightened configuration; and a rib wound spirally on the tubular wall at a first pitch along the at least one duct portion, the tubular wall including at least one duct portion and the rib forming at least one connection portion without requiring additional longitudinally extending structure therefrom, wherein the at least one connection portion has a narrower pitch than the duct portions the rib which forms the at least one connection portion is wound at a second pitch which is narrower than the first pitch is at a second pitch which is narrower than the first pitch.

* * * * *